US00PP35600P2

(12) United States Plant Patent
Clark

(10) Patent No.: US PP35,600 P2
(45) Date of Patent: Jan. 23, 2024

(54) ***COLEUS* PLANT NAMED 'UF20-20-5'**

(50) Latin Name: *Coleus scutellarioides*
Varietal Denomination: UF20-20-5

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,901

(22) Filed: Jan. 13, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373
CPC ..... A01H 5/12; A01H 5/00; A01H 6/50
See application file for complete search history.

(56) References Cited

U.S. PATENT DOCUMENTS

PP14,790 P2 * 5/2004 Smith ..... A01H 6/50
Plt./373

OTHER PUBLICATIONS

Germania Lucas Greenhouses 2022 Program 15 retrieved on 815/23 at https://germaniaseed.com/orderforms/2022/lucas_715_2022.pdf, pp. 1-3, 11. (Year: 2022).*

UF/IFAS UF *Coleus* Breeding Program 2022, retrieved on Aug. 15, 2023 at https://hort.ifas.ufl.edu/uf-coleus-breeding-program/our-cultivars/#2022, 2 pp. (Year: 2023).*

* cited by examiner

*Primary Examiner* — June Hwu
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-20-5', selected for its combination of desirable traits that make it well-suited for good performance as an annual plant in the summer landscape. 'UF20-20-5' was selected for its consistent foliage color patterning, and fast growth rate and vigor in the greenhouse and landscape. 'UF20-20-5' has bright greyish red foliage with purplish red centers, yellow green margins, prominent greyish red and purplish red mid-veins, and pale yellow green bases. It is a vigorous plant that easily grows four feet tall in the landscape in one season, maintaining similar color in both sun and shade. 'UF20-20-5' maintains its foliage colors for an entire summer garden season in a broad range of environmental conditions due to the retention of its foliage for an extended period. It has an upright and spreading habit, but it is uniform, growing wider than tall.

5 Drawing Sheets

Genus and species: *Coleus scutellarioides*.
Cultivar denomination: 'UF20-20-5'.

BACKGROUND OF THE NEW CULTIVAR

The invention relates to a new and distinct cultivar of *Coleus* plant named 'UF20-20-5'. The new cultivar 'UF20-20-5' originated from an open pollination conducted in May-November 2019 in Citra, Florida between the female *Coleus* plant 'UF19-36-2' (unpatented) and an unknown male *Coleus* plant. A single seedling was chosen in May 2020 for further asexual propagation in Gainesville, Florida.

The new cultivar 'UF20-20-5' has been reproduced asexually for over 18 months through vegetative meristem tip cuttings and has been found to retain its distinctive characteristics through successive asexual propagations. 'UF20-20-5' was first propagated asexually by vegetative meristem tip cuttings in May 2020 in Gainesville, Florida, and has remained true-to-type since that time.

Plant Breeder's Rights for the new cultivar 'UF20-20-5' have not been applied for, and 'UF20-20-5' has not been made publicly available more than one year prior to the filing date of this application.

When compared to the female parent 'UF19-36-2', 'UF20-20-5' has large highly lobed and ruffled leaves that are longer than they are wide. Leaves of 'UF20-20-5' are predominantly greyish red with purplish red centers, yellow green margins, prominent greyish red and purplish red mid-veins and pale yellow green bases, particularly on older leaves. In contrast, 'UF19-36-2' has smaller leaves that are longer than they are wide, but are colored dark maroon with dark green margins, with no trace of purplish red on any leaves. 'UF20-20-5' has a vigorous upright and spreading growth habit that is well-branched, whereas 'UF19-36-2' is less vigorous, with a more upright habit that does not spread as wide due to less lateral branching.

'UF20-20-5' was selected for its novel bright greyish red foliage with purplish red centers, defined yellow green margins and novel ruffled leaf shape. 'UF20-20-5' is exceptional because it maintains its foliage color in a broad range of environmental conditions. 'UF20-20-5' is a highly branched and compact plant. 'UF20-20-5' has not been observed to flower in any trials to date, thus it retains its foliage longer and provides longer display life in the summer landscape. It is a vigorous cultivar that can easily grow over four feet tall in the landscape, maintaining similar color in both sun and shade. Vegetative cuttings form 'UF20-20-5' form roots in one week and consistently produce vivid colors in the greenhouse.

SUMMARY OF THE INVENTION

The new cultivar 'UF20-20-5' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF20-20-5' when grown under normal horticultural practices in Gainesville, Florida: 'UF20-20-5' has the combination of vigorous, upright and spreading growth habit, excellent heat tolerance, and consistent multi-colored ruffled leaves that are significantly different than other *Coleus* plants; it has superior stability in foliage color in both sun and shade conditions, maintaining stable color in all conditions; 'UF20-20-5 is a vigorous cultivar with excellent lateral branching, making it suitable for propagators and producers; and 'UF20-20-5' has also been observed to have long-season performance in landscape trials in Gainesville, Florida.

DESCRIPTION OF THE FIGURES

This new *Coleus* cultivar 'UF20-20-5' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar;

FIG. 3 shows a close-up view of the foliage of the new *Coleus* cultivar;

FIG. 4 shows the adaxial side of two mature leaves (left) and an immature leaf (right) of the new *Coleus* cultivar, with corresponding RHS color designations; and FIG. 5 shows the abaxial side of two mature leaves (left) and an immature leaf (right) of the new *Coleus* cultivar, with corresponding RHS color designations.

DETAILED BOTANICAL DESCRIPTION OF THE CULTIVAR

Figure 1:
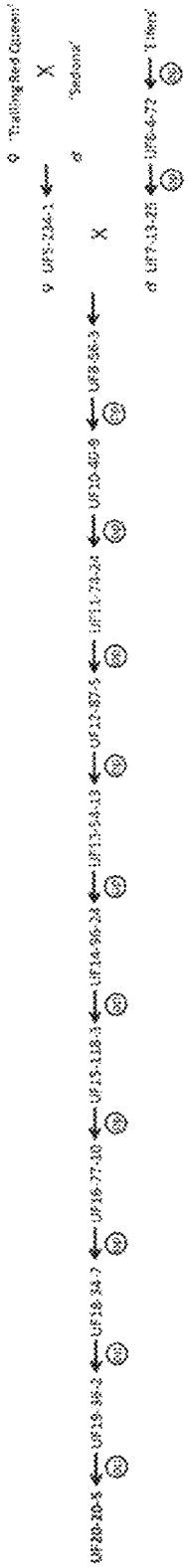
FIG. 1 shows the pedigree of the new *Coleus* cultivar 'UF20-20-5' as shown and described herein, wherein the cultivar 'Sedona' has been patented as U.S. Plant Pat. No. PP14,790 P2 (now expired)
Figure 2:
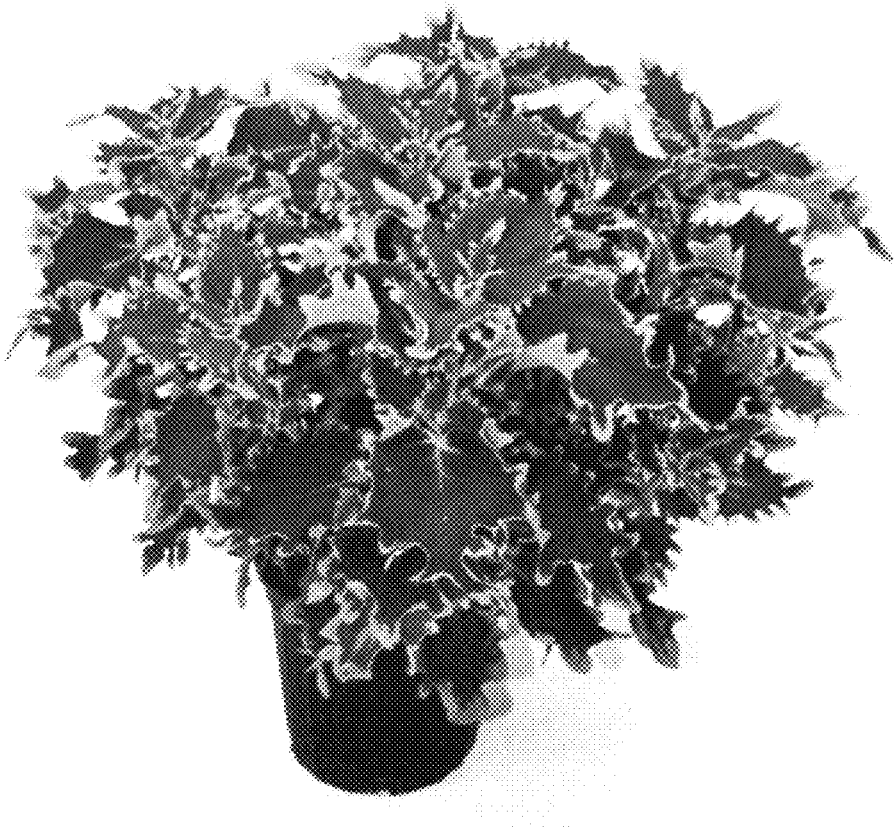
FIGS. 2-5 were taken from plants grown eight weeks from unrooted cuttings in July-September 2022 in a glass-covered greenhouse in Gainesville, Florida.
Figure 3:
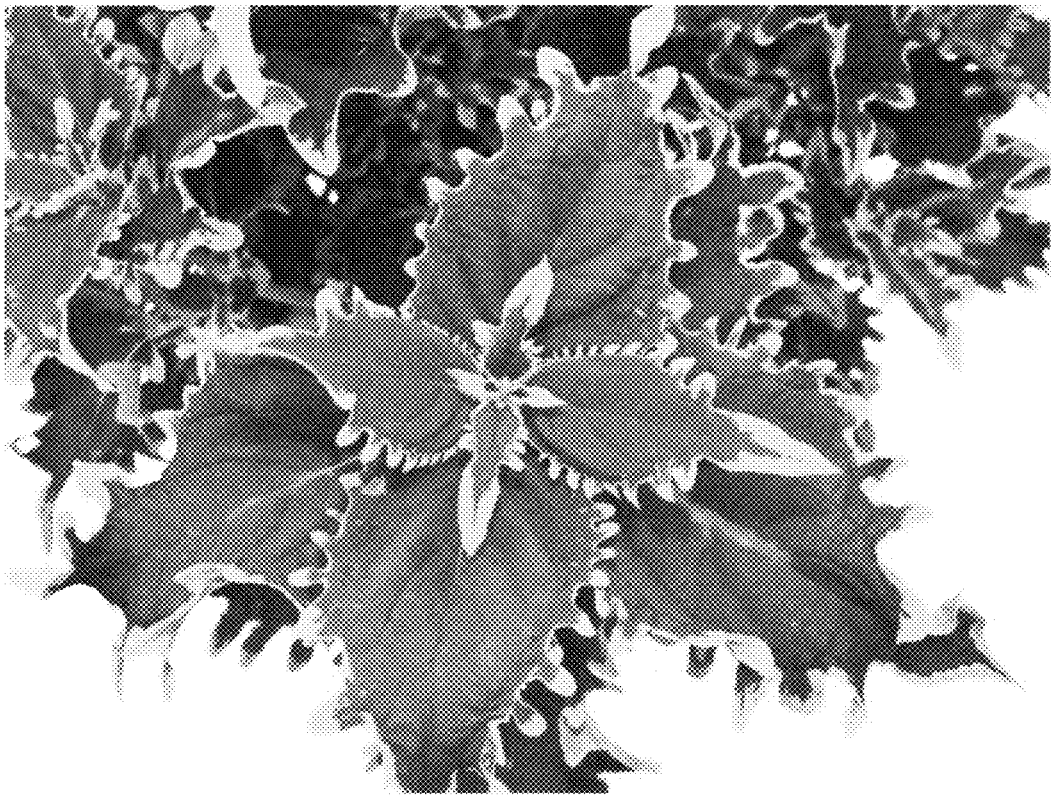
Figure 4:
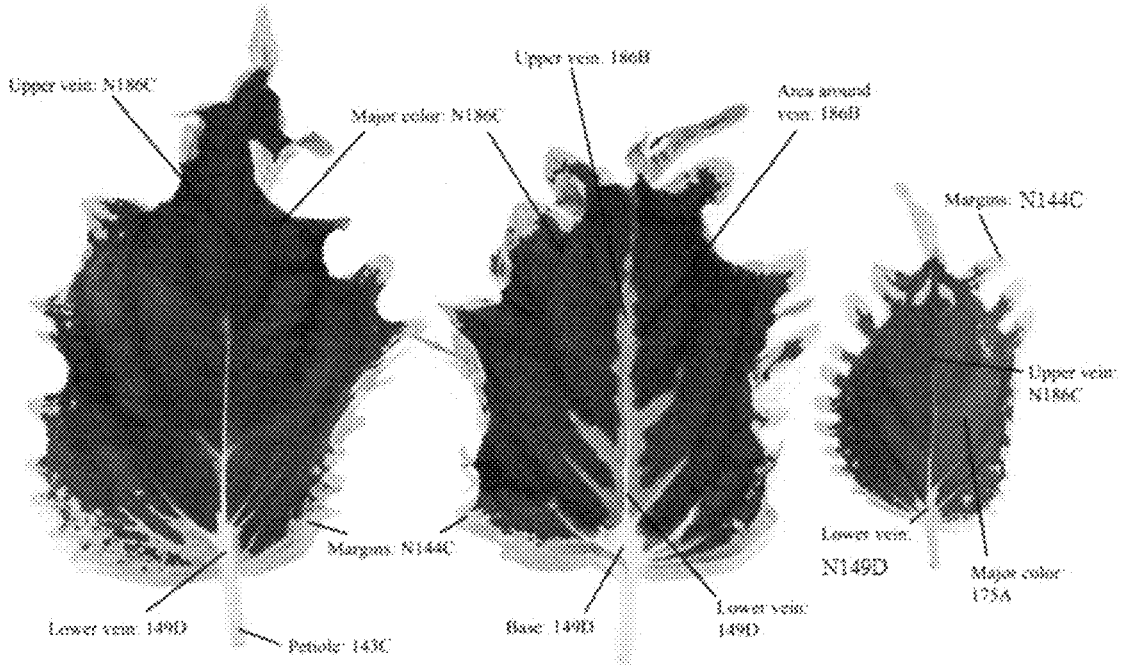
Figure 5:
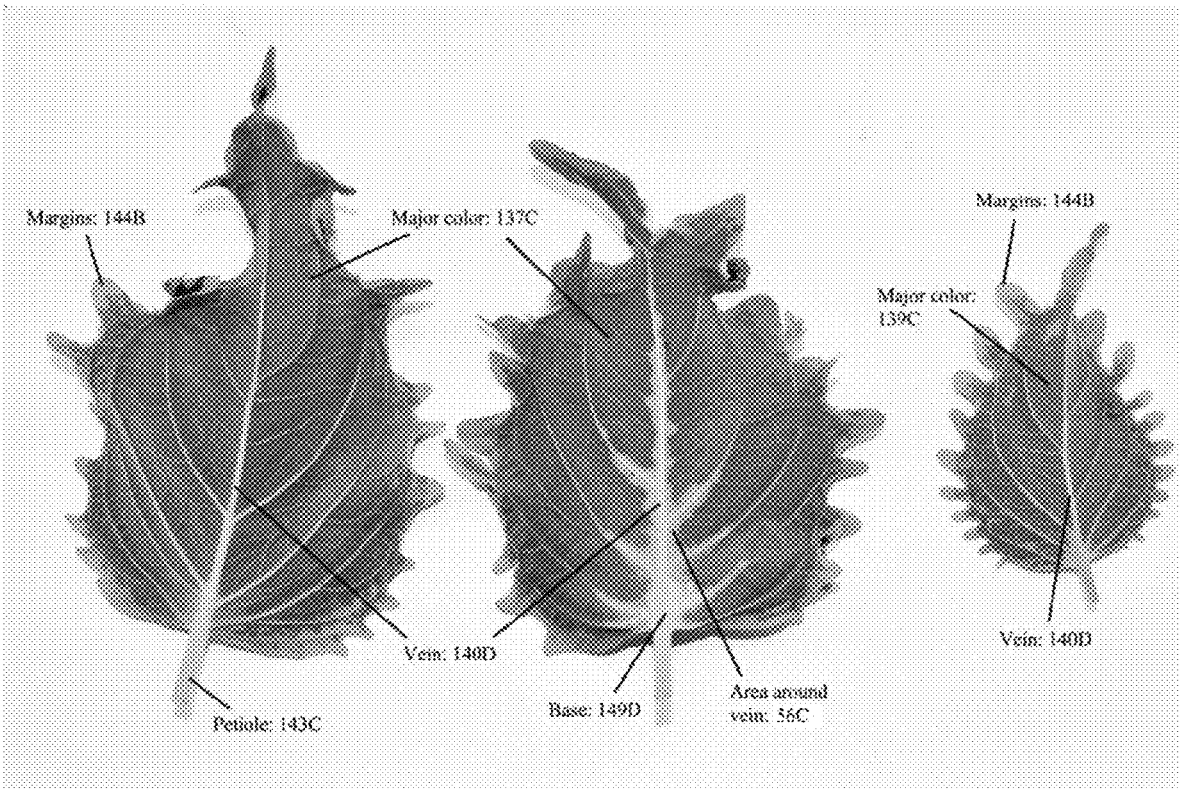

Foliage color was determined under full sun conditions in the middle of the day in a glass-covered greenhouse. Color references are to the RHS Colour Chart of The Royal Horticultural Society of London (RHS), 2007 5th Edition. *Coleus* leaves are rarely one solid color but encompass hues, shades and tints, and color patterns differ from one genotype to another due to varying levels of variegation. The following detailed description of 'UF20-20-5' was obtained using eight-week-old plants grown from unrooted cuttings in July-September 2022 in a glass-covered greenhouse in Gainesville, Florida. The plants were propagated in mist for ten days after cuttings were stuck, then grown in one-gallon pots for approximately six and a half additional weeks.

Botanical Description

Botanical classification:
- *Family.*—Lamiaceae.
- *Botanical name.*—*Coleus scutellarioides.*
- *Common name.*—*Coleus.*
- *Cultivar.*—'UF20-20-5'.

Parentage:
- *Female or seed parent.*—'UF19-36-2'.
- *Male or pollen parent.*—Unknown.

Plant description:
- *Habit.*—Upright and spreading.
- *Height* (*from top of soil*).—30-35 cm.
- *Width* (*horizontal plant diameter*).—70-75 cm.

Propagation:
- *Type cuttings.*—Vegetative meristem tip cuttings having at least 1 node.
- *Time to initiate roots.*—3-4 days.
- *Time to produce a rooted cutting.*—7-10 days.
- *Root habit.*—Fibrous.
- *Root description.*—Callus forms in 2 to 3 days, roots initiate in 3-4 days and become a highly branched cutting in 7-10 days.

Branches:
- *Quantity per plant.*—Approximately 7.
- *Branch color.*—RHS 143B (yellow green).
- *Texture.*—Smooth.
- *Pubescence.*—Not present.
- *Stem description.*—Square-shaped stem.
- *Branch diameter.*—0.7-0.8 cm at the base of a 34-cm-long branch.
- *Branch length.*—34-38 cm.
- *Internode length.*—3-4 cm measured at mid-branch.
- *Anthocyanin.*—Not present.

Foliage description:
- *Quantity of leaves per branch.*—22-23. Arrangement: Opposite.
- *Fragrance.*—Not fragrant.
- *Shape.*—Ovate.
- *Length.*—11-12 cm.
- *Width.*—9-10 cm.
- *Apex.*—Broadly Acute.
- *Base.*—Attenuate.
- *Margin.*—Highly Lobed.
- *Leaf texture.*—Upper surface: Pulverulent. Lower surface: Smooth.
- *Venation color, mature and immature leaves.*—Upper surface, upper vein: RHS N186C (greyish red) and RHS 186B (purplish red). Upper surface, basal region: RHS 149D (pale yellow green). Lower surface: RHS 140D (light yellowish green).
- *Venation pattern.*—Upper surface: Reticulate. Lower surface: Reticulate.
- *Color, immature leaf.*—Upper surface, major color: RHS 175A (reddish brown). Upper surface, margins: RHS N144C (yellow green). Lower surface, major color: RHS 139C (yellow green). Lower surface, margins: RHS 144B (yellow green).
- *Color, mature leaf.*—Upper surface, major color: RHS N186C (greyish red). Upper surface, margins: RHS N144C (yellow green). Upper surface, base: RHS 149D (pale yellow green). Upper surface, around the main vein: RHS 186B (purplish red). Lower surface, major Color: RHS 137C (yellow green). Lower surface, margins: RHS 144B (yellow green). Lower surface, around the main vein: RHS 56C (pale purplish pink).

*Petiole length.*—3.5-4.0 cm.

*Petiole diameter.*—0.3-0.4 cm.

*Petiole color.*—RHS 143C (yellow green).

*Petiole texture.*—Smooth, no pubescence.

Flowers and seeds: Flowers and seeds have not been observed to date during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Comparison with Known Cultivars

When the new cultivar 'UF20-20-5' is compared to the commercial cultivar 'UF16-45-18' (unpatented, commercial name "STAINED GLASSWORKS® Crown Jewel," owned by Dümmen Group B.V., Netherlands), 'UF20-20-5' is superior because 'UF20-20-5' has not been observed to flower in any trials to date, thus it retains its foliage longer and provides longer display life in the summer landscape. In contrast, 'UF16-45-18' is less compact and produces flowers late in the year. 'UF20-20-5' is a vigorous cultivar that can easily grow over four feet tall in the landscape, maintaining similar color in both sun and shade. Vegetative cuttings form 'UF20-20-5' form roots in one week and consistently produce vivid colors in the greenhouse.

What is claimed is:

1. A new and distinct *Coleus scutellarioides* plant named 'UF20-20-5' as shown and described herein.

* * * * *